United States Patent [19]  [11]  4,062,958
Allen, Jr. et al.  [45]  Dec. 13, 1977

[54] METHOD OF TREATING ANXIETY AND COMPOSITIONS THEREFOR

[75] Inventors: George Rodger Allen, Jr., Old Tappan, N.J.; John William Hanifin, Jr.; Daniel Bryan Moran, both of Suffern, N.Y.; Jay Donald Albright, Nanuet, N.Y.

[73] Assignee: American Cyanamid Company, Stamford, Conn.

[21] Appl. No.: 725,598

[22] Filed: Sept. 22, 1976

[51] Int. Cl.² .......................................... A61K 31/495
[52] U.S. Cl. .................................................. 424/250
[58] Field of Search ........................................ 424/250

[56]  References Cited
FOREIGN PATENT DOCUMENTS
839,020  6/1960  United Kingdom.

Primary Examiner—Stanley J. Friedman
Attorney, Agent, or Firm—Edward A. Conroy, Jr.

[57]  ABSTRACT

This disclosure describes compositions of matter useful as anxiolytic agents and the method of meliorating anxiety in mammals therewith, the active ingredient of said compositions of matter being 3-methyl-6-phenyl-1,2,4-triazolo[4,3-b]-pyridazine or a pharmacologically acceptable acid-addition salt thereof.

2 Claims, No Drawings

METHOD OF TREATING ANXIETY AND COMPOSITIONS THEREFOR

BRIEF SUMMARY OF THE INVENTION

This invention relates to novel compositions of matter useful as anxiolytic agents. More particularly, it relates to therapeutic compositions containing 3-methyl-6-phenyl-1,2,4-triazolo[4,3-b]pyridazine or a non-toxic acid-addition salt thereof which meliorate anxiety in mammals. The invention includes the new compositions of matter and the method of meliorating anxiety in mammals therewith. 3-Methyl-6-phenyl-1,2,4-triazolo[4,3-b]pyridazine may be represented by the following structural formula:

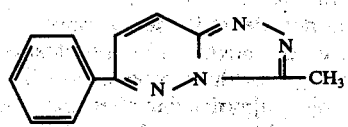

and has been described by Duffin et al. in British Pat. No. 839,020 issued on June 29, 1960.

DETAILED DESCRIPTION OF THE INVENTION

3-Methyl-6-phenyl-1,2,4-triazolo[4,3-b]pyridazine and its non-toxic acid-addition salts have been found to be highly useful for meliorating anxiety in mammals when administered in amounts ranging from about 0.03 milligram to about 10.0 mg. per kilogram of body weight per day. A preferred dosage regimen for optimum results would be from about 0.1 mg. to about 5.0 mg. per kilogram of body weight per day, and such dosage units are employed that a total of from about 7.0 milligram to about 0.35 gram of the active ingredient for a subject of about 70 kg. a body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of fiom about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. 3-Methyl-6-phenyl-1,2,4-triazolo-[4,3-b]pyridazine and its salts are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally admininstered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 0.1 to 5.0 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

3-Methyl-6-phenyl-1,2,4-triazolo[4,3-b]pyridazine forms non-toxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free base is equivalent to its non-toxic acid-addition salts.

The active compound of the present invention possesses central nervous system activity at a non-toxic dose and as such is useful as an anxiolytic agent. That is, it produces certain responses in standard tests with laboratory animals which are known to correlate well with relief of anxiety in man. The compound has been tested pharmacologically and found to have such properties with a desirable wide spread between doses producing anxiolytic activity and toxic symptoms.

The anti-anxiety properties of the active compound of the present invention has been established in a test which indicates anxiolytic activity by the measure of protection from convulsions resulting from the administration of pentylenetetrazole. Graded dose levels of the compound of this invention were administered orally, in a 2% starch vehicle, to groups of at least 5 rats. At the estimated time of peak effect, the rats were treated intravenously with pentylenetetrazole at a dose of 21 to 23 mg./kg. of body weight. This dose is estimated to cause clonic seizures in 99% of unprotected rats. The effective dose ($ED_{50}$) of the test compound for protection of 50% of the animals is calculated by the method of D. H. Finney in "Statistical Methods in Biological Assay", Second Edition, Hafner Publishing Co., New York, 1964, pp. 456–457. Representative results are given in the table which follows in comparison with chlordiazepoxide and meprobamate, which were tested in exactly the same manner. It has been reported [R. T. Hill and D. H. Tedeschi, "Animal Testing and Screening Procedures in Evaluating Psychotropic Drugs" in An Introduction of Psychopharmacology, Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals.

Table I

Protection Against Clonic Seizures Caused By Pentylenetetrazole In Rats

| Compound | Medium Effective Oral Dose mg./kg. $ED_{50}$ |
|---|---|
| 3-Methyl-6-phenyl-s-triazolo[4,3-b]pyridazine | 3 |
| Chlordiazepoxide | 2.5 |
| Meprobamate | 22 |

Another test which has been used to assess anti-anxiety effects is a non-conditioned passive avoidance procedure described by J. R. Vogel, B. Beer and D. E. Clody, "A Simple and Reliable Conflict Procedure for Testing Anti-Anxiety Agents", Psychopharmacologia, Vol. 21, pp. 1–7 (1971). A conflict situation is induced in rats by a modification of this method. To groups of six naive Sprague-Dawley rats (200-220 grams), previously deprived of water for forty-eight hours and food for 24 hours, are administered graded oral doses of test compound suspended in 2% starch vehicle also containing 2 drops of polyethylene glycol and polysorbate 80, or vehicle alone (controls). At the time of peak effect each rat is placed in a plexiglass box fitted with a drinkometer circuit connected between the stainless steel grid floor and a stainless steel drinking tube inserted in a hole in one of the walls of the box. A stimulator supplying monophasic 60 cycle square wave pulses of 0.2 milliamperes peak intensity, a timer which allows alternate 5 second "shock free" and 5 second "shock available" periods during a 5 minute test period, an electromagnetic counter to count the number of shocks received by the rat during the shock available period and a delay of one half second between the successive shocks are incorporated into the drinkometer circuit. After the rat is placed in the box, it is allowed to explore and drink 10% dextrose solution supplied through the tap. After twenty seconds of continuous unpunished drinking, the timer and drinkometer circuits are activated and 5 second shock free and 5 second shock available periods alternate. The number of shocks received by the rat during a 5 minute test period is recorded. The percentage of rats that receive 9 or more shocks in 4 to 5 minutes at each dose level is used as positive response in calculation of the median effective dose ($ED_{50}$). The estimated ($ED_{50}$) for the compound 3-methyl-6-phenyl-1,2,4-triazolo[4,3-b]pyridazine after one hour from oral administration is 100 mg./kg. In comparison, chlordiazepoxide and meprobamate give a median effective dose ($ED_{50}$) of 9.6 and 51.9, respectively, when tested in exactly the same manner.

The invention will be described in greater detail in conjunction with the following specific examples.

EXAMPLE 1

Preparation of 50 mg. Tablets

| Per Tablet | | Per 10,000 Tablets |
|---|---|---|
| 0.050 gm. | 3-Methyl-6-phenyl-1,2,4-triazolo-[4,3-b]pyridazine | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 3-methyl-6-phenyl-1,2,4-triazolo[4,3-b]pyridazine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 2

Preparation of Oral Suspension

| Ingredient | Amount |
|---|---|
| 3-Methyl-6-phenyl-1,2,4-triazolo[4,3-b]pyridazine | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the 3-methyl-6-phenyl-1,2,4-triazolo[4,3-b]-pyridazine is suspended thereon. The saccharin, sodium benzoate, flavor and dye are added and dissolved. The volume is adjusted to 100 ml. with distilled water. Each ml. of syrup contains 5 mg. of 3-methyl-6-phenyl-1,2,4-triazolo[4,3-b]pyridazine.

EXAMPLE 3

Preparation of Parenteral Solution

In a solution of 700 ml. of propylene glycol and 200 ml. of water for injection is suspended 20.0 grams of 3-methyl-6-phenyl-1,2,4-triazolo[4,3-b]pyridazine with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

We claim:

1. The method of meliorating anxiety in a mammal which comprises administering internally to said mammal an anxiolytically effective amount of 3-methyl-6-phenyl-1;2,4-triazolo[4,3-b]-pyridazine or a pharmacologically acceptable acid-addition salt thereof.

2. A therapeutic composition in dosage unit form useful for meliorating anxiety in mammals comprising from about 0.03 milligram to about 10.0 milligrams per kilogram of body weight per daily dosage unit of 3-methyl-6-phenyl-1,2,4-triazolo[4,3-b]pyridazine or a pharmacologically acceptable acid-addition salt thereof in association with a pharmaceutical carrier.

* * * * *